(12) United States Patent
Schultz et al.

(10) Patent No.: US 9,493,393 B2
(45) Date of Patent: Nov. 15, 2016

(54) SEPARATION OF PROPIONIC ACID FROM ACRYLIC ACID

(71) Applicant: ARCHER DANIELS MIDLAND COMPANY, Decatur, IL (US)

(72) Inventors: Mitchell Jo Schultz, Decatur, IL (US); Thomas P. Binder, Decatur, IL (US); Naveen Sudharsan, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 14/906,052

(22) PCT Filed: Aug. 22, 2014

(86) PCT No.: PCT/US2014/052239
§ 371 (c)(1),
(2) Date: Jan. 19, 2016

(87) PCT Pub. No.: WO2015/031182
PCT Pub. Date: Mar. 5, 2015

(65) Prior Publication Data
US 2016/0176798 A1    Jun. 23, 2016

Related U.S. Application Data

(60) Provisional application No. 61/870,906, filed on Aug. 28, 2013.

(51) Int. Cl.
| | | |
|---|---|---|
| C07C 51/47 | (2006.01) |
| C07C 67/56 | (2006.01) |
| C07C 51/36 | (2006.01) |
| C07C 51/377 | (2006.01) |
| C07C 67/303 | (2006.01) |
| B01D 15/38 | (2006.01) |
| C07B 63/00 | (2006.01) |
| B01D 15/18 | (2006.01) |
| B01D 15/36 | (2006.01) |
| C07C 67/317 | (2006.01) |
| C07C 45/52 | (2006.01) |
| C07C 51/215 | (2006.01) |
| C07C 51/25 | (2006.01) |

(52) U.S. Cl.
CPC ........... *C07C 51/47* (2013.01); *B01D 15/1821* (2013.01); *B01D 15/364* (2013.01); *C07B 63/00* (2013.01); *C07C 45/52* (2013.01); *C07C 51/215* (2013.01); *C07C 51/252* (2013.01); *C07C 51/36* (2013.01); *C07C 51/377* (2013.01); *C07C 67/303* (2013.01); *C07C 67/317* (2013.01); *C07C 67/56* (2013.01)

(58) Field of Classification Search
CPC .............................. C07C 51/47; C07C 51/43
See application file for complete search history.

(56) References Cited

PUBLICATIONS

Lavi et al, ISR Analytica, Determination of Propionic and Acrylic Acids by Isocratic Liquid Chromatography. Combination of Reversed Phase Separation, Anion Suppression and Conductivity Detection, 2008, p. 1, recovered from isranalytica.org.il/Isranalytica2008/Posters/Borojovich%20A.doc.*

Nyers et al, Chromatographia, High-Performance Liquid Chromatographic Determination of Monomeric Sodium Acrylate and Acrylic Acid in Polyacrylic Gelling Agents, 1988, 25(10), pp. 915-916.*

* cited by examiner

*Primary Examiner* — Paul A Zucker
(74) *Attorney, Agent, or Firm* — William B. Miller (57) ABSTRACT

A process is provided for chromatographically separating propionic acid from acrylic acid. By means of the inventive process, a reduced propionic acid content acrylic acid product is enabled having a propionic acid content comparable to acrylic acid products from the conventional two stage oxidation of propylene, but wherein the acrylic acid has been produced with a higher propionic acid content by alternative methods.

23 Claims, 5 Drawing Sheets

SEPARATION OF PROPIONIC ACID FROM ACRYLIC ACID

CROSS-REFERENCE TO RELATED APPLICATIONS

This application claims the benefit of provisional application U.S. Ser. No. 61/870,906, filed Aug. 28, 2013 for "Separation of Propionic Acid from Acrylic Acid by Chromatography".

BACKGROUND

Acrylic acid is an important industrial chemical that is used in multiple applications in the polymers industry as well as in other contexts, and acrylic acid and its esters (acrylates) are produced globally in the hundreds of thousands of tons annually. Acrylic acid is conventionally produced by oxidative processes and a variety of feedstocks are known from which acrylic acid may be produced by single or multistage oxidations. Most acrylic acid is produced commercially from propylene, but with increased supplies of inexpensive and abundant natural gas in recent years, propane has attracted increased interest as a feedstock for direct conversion to acrylic acid as have biobased or renewably sourced materials.

With respect first to the biobased or renewably sourced feed-based routes, a number of references describe methods for converting glycerol to acrylic acid and/or acrylates, commonly using glycerol such as that produced in the making of biodiesel (fatty acid methyl esters) from plant oils, see, e.g., U.S. Pat. No. 7,396,962 to DuBois et al. and references cited therein.

A number of efforts have likewise been made to develop processes for making acrylic acid from carbohydrate and/or carbohydrate-derived feedstocks. One feedstock that can be derived from carbohydrates and that has been closely evaluated is 3-hydroxypropionic acid, or 3-HPA. U.S. Pat. No. 2,859,240 to Holmen (1958) indicates that the dehydration of 3-HPA is a "comparatively simple and economical process", but concludes that "the starting material is neither low in cost or readily available in quantity" (col. 1, lines 55-58) Essentially the same assessment is offered 45 years later, wherein in Kumar et al., "Recent advances in biological production of 3-hydroxypropionic acid", Biotechnology Advances, vol. 31, pp. 945-961 (2013), the authors conclude despite "significant progress" in the preceding decade toward "commercial production . . . in the near future" that "many important issues still remain and require more extensive investigations."

Another feedstock that can be derived from carbohydrates and that has been the subject of considerable research as well is lactic acid. In the same 1958 Holmen patent, for example, lactic acid is indicated as having been recognized for some time as preferable to 3-HPA as a prospective feedstock due to its ready availability (referencing a 1950 review of efforts to that time to develop processes for converting lactic acid and the lower alkyl esters of lactic acid to acrylic acid and the corresponding lower alkyl esters of acrylic acid). A commercially viable process yet remains elusive as well for the conversion of lactic acid to acrylic acid, as evidenced by a number of ongoing applications for patent that have recently been filed.

WO 2012/033845 to Ozmeral et al, WO 2012/156921 to Dongare et al. and WO 2013/155245 to Lingoes et al. are representative of these ongoing efforts to develop a commercially viable process for converting lactic acid (and/or lactate esters) to acrylic acid (and/or the corresponding acrylate esters), and each in turn reviews a fairly substantial body of additional published art detailing prior work toward the same objective.

In WO 2012/033845, a fermentation broth containing ammonium lactate is described as processed according to one of four pathways to produce acrylic acid esters. In a first pathway, lactic acid is first purified from the fermentation broth. The highly purified lactic acid is then subjected to a vapor phase dehydration reaction at elevated temperatures and in the presence of an appropriate catalyst to produce acrylic acid, which in turn is esterified in the presence of an esterification catalyst to provide the acrylate esters. In a second pathway, lactic acid in the fermentation broth is dehydrated "without much purification", followed by an esterification to produce acrylic acid esters. In the third pathway, ammonium lactate in the fermentation broth is subjected to simultaneous dehydration and esterification reactions to produce an acrylic acid ester product, while in the fourth pathway, ammonium lactate in the fermentation broth without much purification is subjected first to an esterification reaction to produce a lactic acid ester, and then this lactic acid ester is dehydrated to provide an acrylic acid ester product. In a "most preferred" embodiment according to this fourth pathway, a fermentation broth containing ammonium lactate is concentrated by evaporation of water and subjected to esterification with a C1-C10 alkyl alcohol, preferably in the absence of any exogenous esterification catalyst. Ammonia released during the concentration process is captured for recycling to the lactic acid fermentation, along with further ammonia released during the esterification reaction. The lactic acid ester obtained in the first stage is then dehydrated to produce a corresponding acrylic acid ester.

In WO 2012/156921 to Dongare et al., a catalyst with improved selectivity to acrylic acid from lactic acid and reduced production of acetaldehyde and other products is offered for use in the dehydration of lactic acid to acrylic acid, comprising a calcium phosphate in a calcium to phosphate ratio of from 1.5 to 1.9 as optionally modified with 5 weight percent of sodium. The process is described as involving preheating the catalyst in a fixed-bed reactor at a temperature of 370 to 380 degrees Celsius for from 20 to 40 minutes under highly pure nitrogen, then passing 50-80 wt. pct preheated vapors of a lactic acid solution through a quartz fixed catalyst bed reactor by means of a nitrogen carrier gas. Reported lactic acid conversion under these conditions was 100 percent, with 60 to 80 percent selectivity for acrylic acid and about 15-35 percent selectivity for acetaldehyde.

In WO 2013/155245 to Lingoes et al., reference is made initially to research by a number of parties of a similar character to that reported in Dongare et al., which research confirmed that phosphate and nitrate salts may desirably change the surface acidity of acidic catalysts to inhibit the decarbonylation/decarboxylation of lactic acid to acetaldehyde in particular.

Lingoes et al. contend that even with a reduced selectivity to acetaldehyde, nevertheless even the reduced amounts are problematic, as byproducts can be deposited on the catalyst and result in fouling and in premature and rapid deactivation of the catalyst. Further, once deposited, the byproducts can catalyze other undesired reactions, for example, polymerization reactions (para.0005).

As well, apart from the difficulties caused by being deposited on the catalyst in question, Lingoes et al. point out the difficulties even very small amounts of byproducts such as acetaldehyde, propanoic (or propionic) acid, carbon monoxide, carbon dioxide, 2-3-pentanedione and lactic acid oligomers can cause in processing acrylic acid from the then-known lactic to acrylic processes to make superabsorbent polymers, such that a significant body of literature existed around removal of these impurities from the acrylic acid.

Lingoes et al. reference U.S. Pat. No. 6,541,665 and US Published Pat. Appl. 2011/0257355 as exemplars of this body of literature. In U.S. Pat. No. 6,541,665, a 5-stage crystallization (containing two purification stages and three stripping stages) was effective to obtain 99.94% acrylic acid containing 2600 parts per million by weight of acetic acid and 358 ppm of propionic acid, among other species. In US 2011/0257355, a method is described of removing propionic acid in a single pass crystallization from a crude reaction mixture derived from glycerol dehydration/oxidation to obtain 99% acrylic acid. According to Lingoes et al, prior to their improved catalyst and process, the prior art methods for converting lactic acid to acrylic acid produced amounts of byproducts that were too high ("far too high") to even utilize such purification methods.

With respect to the use of propane rather than propylene as a feed for the production of acrylic acid, U.S. Pat. No. 7,795,470 to Dieterle et al. provides an example of the further work that has been undertaken on this particular alternative approach, and contains a lengthy review of still earlier efforts.

In Dieterle et al, a method is described for the heterogeneously catalyzed partial direct oxidation of propane to acrylic acid in the gas phase, in which n-propane, molecular oxygen and at least one inert diluent gas but including not more than 1 mol percent of cyclopropane are fed to a reactor and passed through a catalyst bed comprising a catalyst in the solid state of aggregation to convert n-propane to an acrylic acid product, and the acrylic acid product is purified by at least two separation zones. In a first separation zone, acrylic acid present in the gaseous product from the reactor is converted to the liquid phase, and the remaining gaseous residual product gas mixture comprising n-propane and depleted in acrylic acid is removed from the first separation zone for recycling at least a part of the n-propane to the reactor, while acrylic acid is separated from the remainder of the liquid phase from the first separation zone in a second separation zone using at least one thermal separation method which comprises at least one isolation of acrylic acid by crystallization. Dieterle et al. explain that propane as produced from natural gas processing includes other constituents that can account for up to 10% by volume and more of the total volume of the crude propane, referencing WO 2006/120233 to Diefenbacher et al., which itself describes certain methods for removing constituents that cause difficulties in the conventional propylene oxidation processes. Dieterle et al. purportedly found that cyclopropane, though an isomer of propylene and behaving like propylene chemically in certain contexts, nevertheless formed propionic acid in their propane to acrylic acid method and could be accommodated only to a limited extent.

As is immediately evident from the foregoing review of the prior art, one challenge common to each of these propylene-alternative methods—whether employing propane or one of the biobased feed-based alternatives—is the presence in the crude acrylic acid products provided by these various alternative methods of assorted impurities.

Acetic acid and propionic acid are recognized as particularly problematic in that both are saturated and cannot be polymerized, so that depending on the polymerization process involved and the applications targeted for the polymer, these impurities may remain in the finished product and risk conferring undesirable corrosive properties on the finished product or being reencountered as waste in the liquid or gaseous discharges from the polymerization process. Commercial acrylic acid processes proceeding from propylene via a two stage oxidation typically yield propionic acid concentrations of not more than approximately 1,000 parts per million by weight. Unfortunately, however, acrylic acid produced from glycerol typically contains at least about five times this much propionic acid (according to U.S. Pat. No. 8,440,859 to Dubois, assigned to Arkema France) and acrylic acid from propane may contain from three to thirty times the amount produced in a typical propylene-based process (according to EP 2039674 B1 to Han et al., assigned to Rohm and Haas Company). For acrylic acid from lactic acid, Lingoes et al. claim to have been the first to produce acrylic acid from lactic acid with low enough byproducts for further purification methods—costly as they might be, for example, multistage crystallization—to be sufficient to achieve a commercially acceptable glacial acrylic acid purity, yet Lingoes et al. describe their process as being preferably "sufficient" "to produce propanoic acid in a molar yield of less than about 6%, more preferably less than about 1%" and in fact show a substantial deterioration in performance in a number of respects, including byproduct make, unless quartz reactors were used.

Further, while additional acetic acid from glycerol-, lactic- or propane-based processes can be removed to an extent in a light fraction by conventional distillation methods, the boiling points of propionic and acetic acids are virtually identical so that separation by distillation of the excess propionic acid is not really possible. As well, propionic and acrylic acids have similarly solubilities in the solvents that have commonly been considered for solvent extraction, so this method has heretofore not been successfully used as a means to separate the propionic acid byproduct from the crude acrylic acid product to make a glacial acrylic acid product of acceptable purity.

According to the above-mentioned EP 2039674 B1 to Han et al, claiming priority from September 2007 and published as of Mar. 25, 2009, the only commercial technique available for effectively separating propionic acid from acrylic acid is melt crystallization as described in U.S. Pat. No. 5,504,247 to Saxer et al. (Sulzer Chemtech AG). This approach is however very capital- and energy-intensive. An alternative approach acknowledged by Han et al. would involve a selective reduction of propionic acid in the presence of a catalyst, but the one example acknowledged by Han et al. from the prior art (from JP 2000053611) concurrently showed an undesirable yield loss of up to 8.6 percent of acrylic acid that was oxidized in reducing the propionic acid content from 337 ppm to 115 ppm, using a MoFeCoO catalyst.

Han et al. propose an improved catalyst and method for the selective reduction of propionic acid, wherein a mixed metal oxide catalyst of the formula $A_aM_bN_cX_dZ_eO_f$ is used, where A is "at least one element selected from the group consisting of Mo and W; M is at least one element selected from the group consisting of V and Ce; N is at least one element selected from the group consisting of Te, Sb and Se; X is at least one element consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu; and Z is at least one element selected from the group consisting of Zn, Ga, Ir, Sm, Pd, Au, Ag, Cu, Sc, Y, Pr, Nd and Tb; and O is oxygen in oxide form and wherein, when a=1, b=0.01 to 1.0, c=0.01 to 1.0, d=0.01 to 1.0, e=0 to 0.1, and f is dependent on the oxidation state of the other elements". Preferred catalysts were "$Mo_aV_mTe_n$-$Nb_xO_o$ and $W_aV_mTe_nNb_xO_o$ wherein a, m, n, x and o [sic—f?] are as previously defined". Han et al.'s catalyst exhibited reduced acrylic acid yield losses, but the losses were still substantial, being "only" about 6 percent.

US Published Patent Applications 2013/0267735 and 2013/0274509, both to Han et al. and both claiming the same priority and PCT filing dates, briefly describe additional methods for reducing the amount of propionic acid produced in the process of oxidizing propane to acrylic acid. In the former, a reduced amount of steam is employed to reduce the amount of propionic acid produced in the oxidation. While steam is acknowledged as necessary for the economical conversion of propane to acrylic acid, and while "some" acrylic acid yield is lost with reduced steam levels, yet Han et al observe that "the economic benefit derived from reducing the capital and operating costs of the process required to separate PA [propionic acid] from the final product can offset the yield loss." The latter filing indicates that the amount of propionic acid produced in the oxidation can also be reduced by using a reactor with an L/D ratio greater than 10, and preferably in the range of from 20 to 40, and by carrying out the process virtually isothermally. The example of the '509 application more particularly shows a reduction in propionic acid make from 1500 ppm to 950 ppm by employing a reactor (0.25 inch OD) that was 4 times as long as the reactor for a comparative example, and operated within a two degree temperature range throughout its length as compared to a 42 degree range for the comparative example. Interestingly, the latter filing contains no similar concession of acrylic acid yield loss, though the sole example provided in the '509 application uses a reduced amount of steam in line with the '735 application and in fact appears to directly correspond with Example 2 of the '735 application, wherein reduced propionic acid make is said to be achieved with some sacrifice of acrylic acid make.

The above-referenced U.S. Pat. No. 8,440,859 to Dubois adopts an entirely different approach in view of the significant additional production of propionic acid in Arkema's process for making biobased acrylic acid from glycerol, describing their solution as a method for producing a bioresourced propionic acid product from glycerol that is sufficiently concentrated to be used in the same applications as propionic acid from a propylene-based process, see col. 3, lines 50-54. Cited applications include use as a solvent, as a food preservative, in herbicide manufacture and in the preparation of vinyl propionate monomer for certain polymer applications, col. 1, lines 15-19. In Dubois's method, the mother liquor from a melt crystallization purification method of the type described in U.S. Pat. No. 5,504,247 is hydrogenated to convert acrylic acid retained in the mother liquor to propionic acid.

A better solution is clearly needed, particularly in the context of processes for making biobased acrylic acid (whether from glycerol, lactic acid or some other material or combination of materials) or for making acrylic acid from propane, wherein excessive propionic acid is generated or wherein acceptable propionic acid generation requires concessions in the amount of acrylic acid that can be made. "Biobased" as used herein, it should be noted, means and refers to those materials whose carbon content is shown by ASTM D6866 to be derived from or based in significant part (at least 20 percent or more) upon biological products or renewable agricultural materials (including but not being limited to plant, animal and marine materials) or forestry materials. "Wholly biobased" thus will be understood as referring to materials whose carbon content by ASTM D6866 is entirely or substantially entirely (for example, 95 percent or more) indicated as of biological origin.

In this respect ASTM Method D6866, similar to radiocarbon dating, compares how much of a decaying carbon isotope remains in a sample to how much would be in the same sample if it were made of entirely recently grown materials. The percentage is called the biobased content of the product. Samples are combusted in a quartz sample tube and the gaseous combustion products are transferred to a borosilicate break seal tube. In one method, liquid scintillation is used to count the relative amounts of carbon isotopes in the carbon dioxide in the gaseous combustion products. In a second method, 13C/12C and 14C/12C isotope ratios are counted (14C) and measured (13C/12C) using accelerator mass spectrometry. Zero percent 14C indicates the entire lack of 14C atoms in a material, thus indicating a fossil (for example, petroleum based) carbon source. One hundred percent 14C, after correction for the post-1950 bomb injection of 14C into the atmosphere, indicates a modern carbon source. ASTM D6866 effectively distinguishes between biobased materials and petroleum derived materials in part because isotopic fractionation due to physiological processes, such as, for example, carbon dioxide transport within plants during photosynthesis, leads to specific isotopic ratios in natural or biobased compounds. By contrast, the 13C/12C carbon isotopic ratio of petroleum and petroleum derived products is different from the isotopic ratios in natural or bioderived compounds due to different chemical processes and isotopic fractionation during the generation of petroleum. In addition, radioactive decay of the unstable 14C carbon radioisotope leads to different isotope ratios in biobased products compared to petroleum products.

SUMMARY OF THE INVENTION

The present invention concerns, in one aspect, a process for chromatographically separating out propionic acid from an acrylic acid composition containing excess propionic acid and for thus providing a reduced propionic acid content acrylic acid product.

In an alternative approach, chromatography is employed in combination with crystallization to remove propionic acid from an acrylic acid composition containing excess propionic acid and to thus provide a reduced propionic acid content acrylic acid product.

In a further variation of a chromatographic or combined chromatographic/crystallization method for producing a reduced propionic acid content acrylic acid product, residual acrylic acid remaining in the propionic acid removed from the acrylic acid composition is hydrogenated to provide additional propionic acid.

In still a further alternative, propionic acid removed from the acrylic acid composition may instead be oxidatively dehydrogenated to yield additional acrylic acid.

According to another aspect, the present invention concerns a process for producing acrylic acid by the direct oxidation of propane, wherein propionic acid produced in the oxidation of propane is removed by chromatography or by a combination of chromatography and crystallization methods to provide a reduced propionic acid content acrylic acid product.

In a variation, residual acrylic acid in the propionic acid so removed is hydrogenated to provide additional propionic acid.

In a further alternative embodiment, the propionic acid so removed is instead oxidatively dehydrogenated to yield additional acrylic acid.

According to yet another aspect, a process is provided for producing biobased acrylic acid from glycerol, wherein excess propionic acid produced with the acrylic acid is removed by chromatography or by a combination of chromatography and crystallization methods to provide a reduced propionic acid content biobased acrylic acid product.

According to still another aspect, a process is provided for producing biobased acrylic acid from lactic acid and/or lactate esters, including without limitation ammonium lactate and the lower alkyl lactate esters that have previously been proposed, wherein excess propionic acid produced with the acrylic acid is removed by chromatography or by a combination of chromatography and crystallization methods to provide a reduced propionic acid content biobased acrylic acid product.

In a variation of either of these biobased acrylic acid processes, residual acrylic acid in the propionic acid so removed is hydrogenated to provide additional propionic acid.

In an alternative, propionic acid removed from the biobased acrylic acid from either of these processes is oxidatively dehydrogenated to yield additional biobased acrylic acid.

DETAILED DESCRIPTION OF PREFERRED EMBODIMENTS

Figure 1:
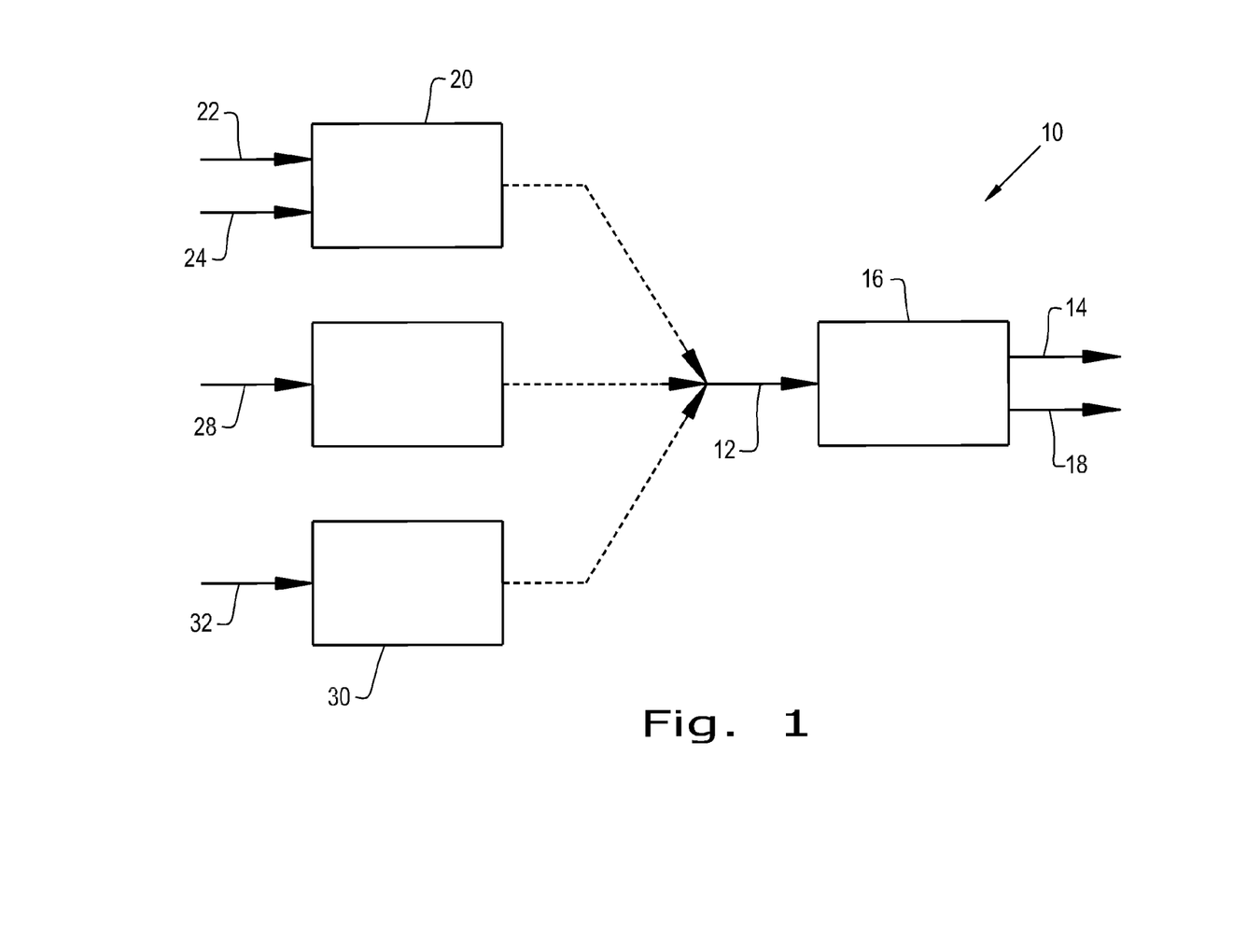
FIG. 1 schematically depicts a process for making a reduced propionic acid content acrylic acid product according to the present invention, wherein the acrylic acid product containing excess propionic acid to be removed is shown as sourced from a) the direct oxidation of propane, b) the dehydration of glycerol to produce acrolein and from the subsequent oxidation of the acrolein to produce acrylic acid, c) the production of lactic acid and/or lactate esters and the subsequent dehydration of the lactic acid and/or lactate esters to form acrylic acid and/or the corresponding acrylate esters or d) a combination of these source processes.

Turning now to FIG. 1, a process 10 is schematically depicted wherein an acrylic acid product 12 containing excess propionic acid is processed by means of chromatography or by applying a combination of chromatography and crystallization to remove the excess propionic acid 14 in a propionic acid removal step 16 and thereby provide a reduced propionic acid content acrylic acid product 18. In one embodiment, the acrylic acid product 12 containing excess propionic acid is obtained from a process 20 whereby propane 22 is converted to acrylic acid by direct oxidation with an oxygen source 24. In another embodiment, the acrylic acid product 12 is obtained from an upstream process 26 for converting glycerol 28 to acrylic acid. In still another embodiment, the acrylic acid product 12 is obtained from a process 30 for converting lactic acid and/or lactate esters 32 to acrylic acid. In yet other embodiments, the acrylic acid product 12 is obtained from a combination of two or all three of the processes 20, 26 and 30.

Where the acrylic acid from two or all three of the source processes 20, 26 and 30 is processed according to the present invention to remove excess propionic acid therefrom, it will be understood, parenthetically, that the acrylic acid from the respective source processes may be processed independently (individual acrylic acid products 12), or may be combined from any two or more of the source processes 20, 26 and 30 (a fully combined acrylic acid product drawing from all three source processes, or a combined acrylic acid product 12 from two processes with an individual acrylic acid product 12). As a general matter, however, it is expected that it will be preferable to combine acrylic acid from any of the source processes 20, 26 and 30 in concurrent practice at a given location or facility in a single combined acrylic acid product 12 as suggested by FIG. 1.

An extensive review of the known processes 20, 26 and 30 need not be undertaken herein, as the acrylic acid products produced from any of these should be amenable to treatment by chromatography or by a combination of chromatography and crystallization methods as described and exemplified herein to remove excess propionic acid, though certainly it will be expected that the acrylic acid product generated by one propane oxidation process 20, for example, may differ from that generated by another process 20 for producing acrylic acid from propane. Accordingly, while it can likewise be expected that the manner in which an acrylic acid product 12 from one process 20 is ideally processed according to the present invention may differ from the manner in which another process 20 is ideally processed, yet it is considered that those skilled in the art will be well able to determine how particular products 12 (or combinations of such products 12) should be processed by chromatography or by a combination of chromatography and crystallization to provide a desired reduced propionic acid acrylic acid product 18.

Nevertheless, it is appropriate herein to briefly reference some of the known processes 20, 26 and 30, if only to illustrate the extent to which research and development efforts have continued for providing a viable alternative to the long-known and widely-practiced propylene-based methods, both from propane as a conventional, fossil fuel-based alternative feedstock and from the various biobased feeds that have been previously mentioned.

Examples of a process 20 for converting propane to acrylic acid can be found in U.S. Pat. No. 7,795,470 to Dieterle et al and in any of the numerous references cited therein, wherein a "crude" propane having not more than a certain percentage of cyclopropane is passed with molecular oxygen and at least one diluent gas in the gas phase and at an elevated temperature through a catalyst bed containing multielement oxides in the solid state of aggregation. US 2013/0144085 to Hazin et al. describes another process embodiment wherein propane is converted to acrylic acid in the presence of a mixed metal oxide catalyst of the formula $MoV_aNb_bPt_cM_dZ_eO_x$ where M is one or more of Ag, Te and Sb, and Z is one or more of Ru, Mn, Sc, Ti, Cr, Fe, Co, Ni, Cu, Zn, Ga, Y, Zr, Rh, Pd, In, Ce, Pr, Nd, Sm, Tb, Ta, W, Re, Ir, Au, Pb and B. U.S. Pat. No. 5,380,933 to Ushikubo et al., EP 1930074 and WO 2006/008177 both to Schlögl et al, and EP 2179793 to Celaya Sanfiz et al also disclose processes using various mixed metal oxide catalysts, while US 2013/0274509 and US 2013/0274509 both to Han et al. (and discussed above) focus on process refinements other than to the catalyst for reducing propionic acid production, using steam and/or a certain L/D ratio in a tubular reactor wherein propane, molecular oxygen and at least one diluent gas are passed through a $MoV_bM^1_cM^2_cO_n$ catalyst, where $M^1$ is at least one of Te and Sb, and $M^2$ is at least one of Nb, Ta, W, Ti, Al, Zr, Cr, Mn, Ga, Fe, Ru, Co, Rh, Ni, Pd, Pt, La, Bi, B, Ce, Sn, Zn, Si and In.

Examples of a process 26 for making biobased acrylic acid from glycerol include a process such as described in U.S. Pat. No. 7,396,962 to Dubois et al., or in any of a number of other recent published patent applications or patents of a similar nature or which are similarly directed and which have been assigned to Arkema France, see, e.g., U.S. Pat. No. 8,212,070 to Dubois et al., U.S. Pat. No. 8,252,960 to Dubois et al., U.S. Pat. No. 8,378,136 to Dubois, U.S. Pat. No. 8,530,697 to Patience et al., U.S. Pat. No. 8,609,893 to Lozowski et al., and US Pub. Pat. Appl. US 2014/206527 to Dubois et al.

In U.S. Pat. No. 7,396,962, Dubois et al. review several older references describing methods for dehydrating glycerol to the same acrolein intermediate as found in a conventional gas-phase process for making acrylic acid from propylene, including U.S. Pat. No. 5,387,720 to Neher et al., wherein glycerol is dehydrated to acrolein in either a liquid phase or a preferred gas phase process over acidic solid catalysts having a Hammett acidity of less than +2 and preferably less than −3. Suitable catalysts include natural or synthetic siliceous materials, e.g., mordenite, montmorillonite and acidic zeolites; supports in the form of oxides or siliceous materials, such as alumina or titania, coated with mono-, di- or triacidic inorganic acids; oxides or mixed oxides such as gamma-alumina, mixed $ZnO/Al_2O_3$ or heteropolyacids. Dubois et al. indicate that in Neher et al's process, however, phenol and polyaromatic byproducts are formed which tend to cause coking of the catalyst, and that other byproducts such as hydroxypropanone or propanaldehyde are formed which are removed with difficulty. In this particular patent to Dubois et al., improvement is claimed in these respects through supplying molecular oxygen to the dehydration reaction, so that these problematic byproducts are formed to a lesser degree.

U.S. Pat. No. 8,212,070 to Dubois et al. describes a method for preparing acrylic acid from an aqueous glycerol solution, which involves a first dehydration step carried out in the gas phase in the presence of an effective dehydration catalyst and under a pressure of between 1 and 5 bar, an intermediate purification step wherein water and heavy byproducts from the dehydration step are at least partly condensed out before an oxidation step wherein acrolein is oxidized to acrylic acid.

U.S. Pat. No. 8,252,960 to Dubois et al. concerns the dehydration of glycerin in the presence of a catalyst comprising mainly a compound in which protons in a heteropolyacid are exchanged at least partially with at least one cation selected from elements belonging to Group1 to Group 16 of the Periodic Table of Elements. Higher acrolein yields are claimed to result.

U.S. Pat. No. 8,378,136 to Dubois describes a process for preparing acrolein from an aqueous solution of glycerol through a gas phase dehydration using a different catalyst, namely, a catalyst system comprising oxygen, phosphorus and at least one metal chosen from vanadium, boron or aluminum.

U.S. Pat. No. 8,530,697 to Patience et al. concerns a method for the reactive vaporization of aqueous solutions of glycerol in a fluidized bed containing a reactive solid, which is claimed to make possible the simultaneous vaporization of an aqueous solution of glycerol, the removal of impurities present in the glycerol solution or that are generated in the evaporation, as well as the dehydration to acrolein and/or the oxydehydration of glycerol to acrylic acid.

U.S. Pat. No. 8,609,893 to Lozowski et al. describes a method for removing heavier-than-water organic compounds from a process for dehydrating glycerol to acrolein and then producing acrylic acid from the acrolein, so that a recycle stream can be generated that can be recycled back to the dehydration stage without the accumulation of heavy impurities in the process as a whole and so that the consumption of water and discharge of polluted aqueous streams can be reduced.

In US 2014/206527 to Dubois et al. concerns a further alternative glycerol dehydration catalyst and a method of making the same, wherein the catalyst comprises a carrier including at least one metal oxide selected from $TiO_2$, $SiO_2$, $Al_2O_3$, $ZrO_2$, and $Nb_2O_5$, which carrier is characterized by a bimodal porous structure in which the volume ratio between a pore volume of mesopores having a pore size of more than 2 nm to less than 50 nm to a pore volume of macropores having a pore size of 50 nm or more is equal to or more than 0.5, and wherein the carrier supports a W-containing metal oxide or a metal oxide containing at least one of P, Si, Mo and V in addition to the W-containing metal oxide.

Not surprisingly, Arkema has not been alone in recent efforts to develop a commercial process for making acrylic acid from glycerol via an acrolein intermediate. U.S. Pat. No. 8,530,703 to Strohm et al. (Battelle Memorial Institute) thus describes the dehydration of glycerol using a catalyst comprising a fumed support material such as fumed silica, phosphate, and at least one or more metals from Groups 2-12 of the Periodic Table of the Elements and/or Rb, K, and Cs, as well as methods for decoking and regenerating the catalyst. U.S. Pat. No. 7,951,978 to Arita et al. (Nippon Shokubai Co., Ltd) describes a process for dehydrating glycerol to acrolein in which the partial pressure of glycerol is maintained in the range of from 0.01 to 30 kPa, based on the reported discovery that the acrolein yield and catalyst lifetime are independent of the amounts of glycerol processed provide the partial pressure of glycerol in the gas phase process is kept in the specified range. U.S. Pat. No. 7,847,131 to Arita et al. describes a process for dehydrating glycerol to acrolein using a catalyst containing a rare earth metal salt crystal of phosphoric acid. CN 103638965 (Fudan University) describes the dehydration of glycerol to acrolein using a hierarchical porous ZSM-5 zeolite catalyst made in the particular manner described in the reference, while CN 101417928 (Jiangsu Polytechnic University) describes a modified zeolite supported heteropolyacid catalyst for glycerol dehydration. IN 02826DE2008 to Deshpande et al. (Council of Scientific and Industrial Research) specifies an H-ZSM-5 molecular sieve catalyst with 0.05 to 7 percent of an active metal component or the H-ZSM-5 molecular sieve, from 5 to 30 percent of amorphous silicon aluminum gel and 0.05 to 7 percent of the active metal component for the dehydration of glycerol. US 2013/0197258 to Lauriol-Garbey et al. (Centre National De La Recherche Scientifique) describes the dehydration of glycerol to acrolein using a catalyst based on zirconium oxide and having an active phase comprising at least one of a) a silicon oxide, zirconium oxide and at least one metal M oxide, where M can be tungsten, cerium, manganese, niobium, tantalum, vanadium and titanium, and b) a titanium oxide, a zirconium oxide and at least one metal M oxide where M can be tungsten, cerium, manganese, niobium, tantalum, vanadium and titanium. US 2013/303801 to Ueda et al. (National University Corporation Hokkaido University, Nippon Kayaku KK) meanwhile describes a glycerol dehydration method wherein a catalyst is prescribed having as its main component a niobic oxide synthesized by a hydrothermal method.

Examples of a process 30 for making biobased acrylic acid from lactic acid and/or lactate esters include the aforementioned WO 2013/155245 to Lingoes et al., which performs a gas-phase dehydration of lactic acid using a mixture of metal-containing phosphate salts "that together provide the catalyst with a very high basicity density and low acidity density". Various combinations of such metal-containing phosphate salts are described. Prior lactic acid dehydrations to yield acrylic acid are also acknowledged by Lingoes et al., including U.S. Pat. No. 4,729,978 to Sawicki and U.S. Pat. No. 4,786,756 to Paparizos et al. which are said to describe acidic catalysts comprised of metal oxide carriers impregnated with monobasic or dibasic potassium phosphate salts or with aluminum phosphate salts. Weiji et al., ACS Catal., Vol. 1, pp. 32-41 (2011) and Huang et al., Ind. Eng. Chem. Res., vol. 49, page 9082 (2010) are cited for teaching the use of phosphate and nitrate salts for modifying acidic dehydration catalysts for reducing yield losses by decarbonylation/decarboxylation of lactic acid to acetaldehyde, while Lin et al., Can. J. Chem. Eng., vol. 86, pp. 1047-1053 (2008) similarly report calcium and cupric sulfate acid catalysts modified with potassium phosphate salts. Other examples include the above-cited WO 2012/033845 to Ozmeral et al. and WO 2012/156921 to Dongare et al.

In WO 2012/033845 to Ozmeral et al., a fermentation broth containing ammonium lactate is described as processed according to one of four pathways to produce acrylic acid esters. In a first pathway, lactic acid is first purified from the fermentation broth. The highly purified lactic acid is then subjected to a vapor phase dehydration reaction at elevated temperatures and in the presence of an appropriate catalyst to produce acrylic acid, which in turn is esterified in the presence of an esterification catalyst to provide the acrylate esters. In a second pathway, lactic acid in the fermentation broth is dehydrated "without much purification", followed by an esterification to produce acrylic acid esters. In the third pathway, ammonium lactate in the fermentation broth is subjected to simultaneous dehydration and esterification reactions to produce an acrylic acid ester product, while in the fourth pathway, ammonium lactate in the fermentation broth without much purification is subjected first to an esterification reaction to produce a lactic acid ester, and then this lactic acid ester is dehydrated to provide an acrylic acid ester product. In a "most preferred" embodiment according to this fourth pathway, a fermentation broth containing ammonium lactate is concentrated by evaporation of water and subjected to esterification with a C1-C10 alkyl alcohol, preferably in the absence of any exogenous esterification catalyst. Ammonia released during the concentration process is captured for recycling to the lactic acid fermentation, along with further ammonia released during the esterification reaction. The lactic acid ester obtained in the first stage is then dehydrated to produce a corresponding acrylic acid ester.

In WO 2012/156921 to Dongare et al., a catalyst with improved selectivity to acrylic acid from lactic acid and reduced production of acetaldehyde and other products is offered for use in the dehydration of lactic acid to acrylic acid, comprising a calcium phosphate in a calcium to phosphate ratio of from 1.5 to 1.9 as optionally modified with 5 weight percent of sodium. The process is described as involving preheating the catalyst in a fixed-bed reactor at a temperature of 370 to 380 degrees Celsius for from 20 to 40 minutes under highly pure nitrogen, then passing 50-80 wt. pct preheated vapors of a lactic acid solution through a quartz fixed catalyst bed reactor by means of a nitrogen carrier gas. Reported lactic acid conversion under these conditions was 100 percent, with 60 to 80 percent selectivity for acrylic acid and about 15-35 percent selectivity for acetaldehyde.

Returning now to FIG. 1, an acrylic acid product 12 (or a plurality of such acrylic acid products 12 obtained from a plurality of source acrylic acid manufacturing processes) containing excess propionic acid is processed by means of chromatography or by applying a combination of chromatography and crystallization to remove the excess propionic acid 14 in a propionic acid removal step 16 and thereby provide a reduced propionic acid content acrylic acid product 18.

Thus, in a first embodiment, propionic acid is removed by chromatography. Continuous industrial-scale adsorption processes are well known for their efficiency. The operation of a continuous countercurrent moving bed chromatographic apparatus in particular enhances the mass transfer driving force, allowing higher processed throughput for a given quantity of adsorbent and a more complete separation of desired components as compared to traditional batch elution chromatography. Nevertheless, in this countercurrent mode of operation both fluid and solid phases must be in motion. The movement of the solids presents considerable technical problems, however, including erosion of the adsorbent (causing fines leading to high pressure drops) and equipment abrasion. Because of these difficulties, simulated moving bed chromatographic systems have been developed wherein the solid adsorbent is kept static but a periodic one-column shift is performed of all inlet as outlet streams in the direction of the fluid flow. In this manner, an apparent or simulated countercurrent movement of the solid is created relative to the fluid flow. Such simulated moving bed chromatographic systems are widely used in a number of industries and for a variety of applications, and are the preferred approach for a process 16 according to this first embodiment, wherein an acrylic acid product 12 is chromatographically separated to remove excess propionic acid and provide a reduced propionic acid content acrylic acid product 18 containing preferably less than about 3000 ppm by weight of propionic acid, and more preferably less than about 1000 ppm by weight of propionic acid.

A detailed treatment of simulated moving bed chromatographic systems, their design and operation need not be undertaken herein, as these systems are in use and well-known; nevertheless, those skilled in the art may find additional information as desired in the open literature, for example, in Gomes and Rodrigues, "Simulated Moving Bed Chromatography: From Concept to Proof-of-Concept", *Chemical Engineering Technology*, vol. 35, No. 1, pp 17-34

(2011) which article is hereby incorporated herein by reference, and will be guided by examples described below.

The just-referenced examples show that amphoteric resins—including both cationic and anionic functional groups attached to a polystyrene matrix—are effective in the process step 16. These resins are typically used for the separation of an electrolyte and non-electrolyte, or for the separation of two electrolytes. Various amphoteric chromatography resins are commercially available in addition to the DIAION AMP-03 amphoteric ion exchange resin sold by Mitsubishi Chemical and employed in several examples below, and may be used. For instance, an earlier version of the same resin was sold under the DIAION AMP-01 tradename and may be commercially available still to an extent; though reportedly of a different and perhaps less uniform bead size, this earlier version of the resin should also be suitable for use in the process step 16.

The DIAION AMP-03 amphoteric ion exchange resin itself is described by its supplier as an amphoteric ion exchange resin in which a quaternary ammonium group and a carboxy group are incorporated on a cross-linked polystyrene frame, having a uniform bead size of 260 µm and outstanding resistance to degradation and leaching. Suggested applications use water as the eluent (mobile phase) to separate various salts in an aqueous solution; accordingly it is expected that in an alternate embodiment, the propionic and acrylic acid (in an acrylic acid product 12 containing excess propionic acid) may be separated using the DIAION AMP-03 amphoteric ion exchange resin or a similar amphoteric resin by forming propionate and acrylate esters from the propionic and acrylic acids in the acrylic acid product 12 and then separating these esters.

Figure 2:
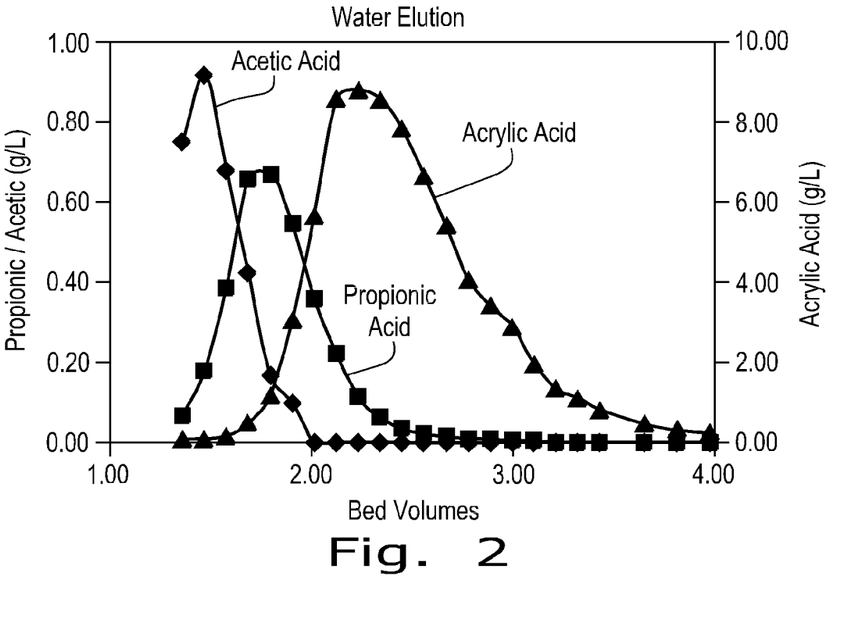
FIG. 2 depicts the results of pulse testing with an amphoteric resin for use in performing a chromatographic separation of excess propionic acid from an acrylic acid product from any of the source processes referenced in FIG. 1, using water as the eluent.
Figure 3:
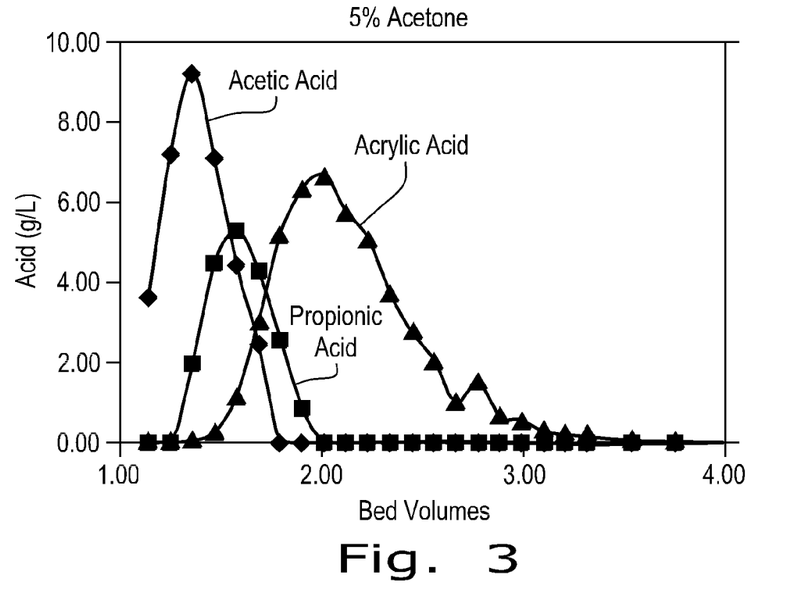
FIG. 3 depicts the results of pulse testing of the same resin system, but using a mixed eluent of 5% acetone in water.
Figure 4:
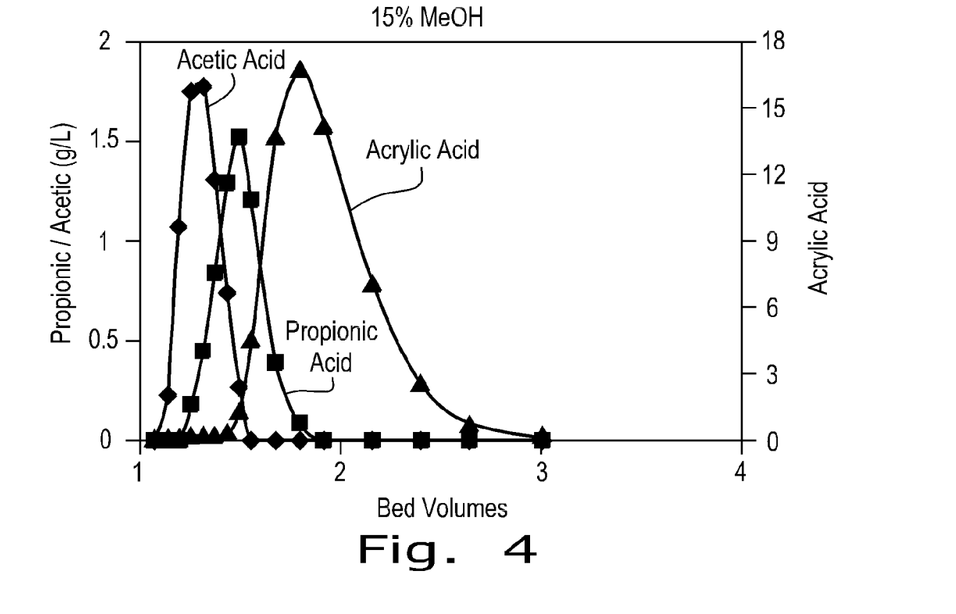
FIG. 4 depicts the results of pulse testing using a methanol co-solvent rather than acetone.
Figure 5:
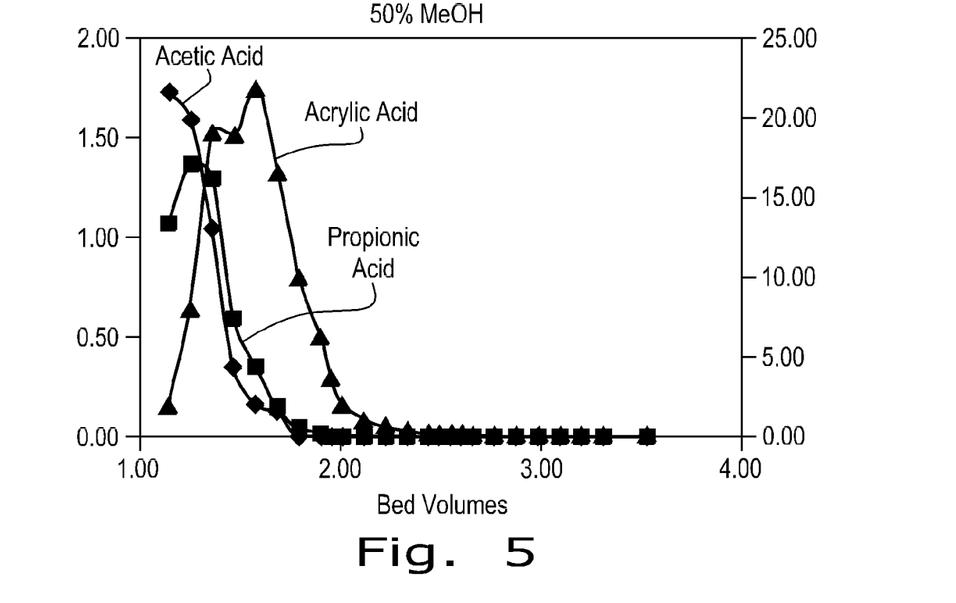
FIG. 5 depicts the results of pulse testing using a higher percentage of the methanol co-solvent.
Figure 6:
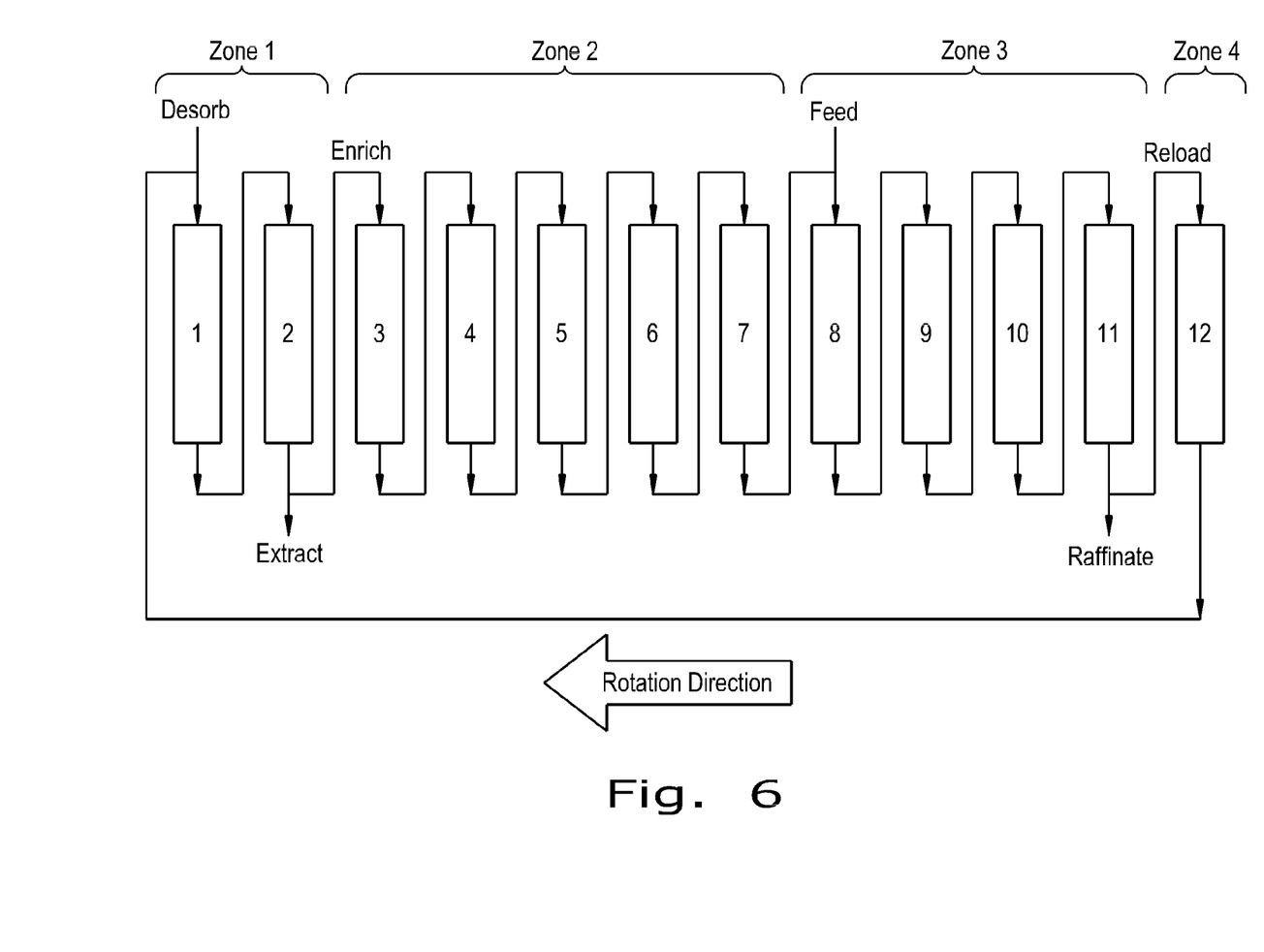
FIG. 6 schematically depicts a 12-column simulated moving bed chromatographic apparatus used in certain of the examples below based on the initial pulse testing.

Using water as the eluent (as suggested by Mitsubishi for the separation of salts) would likely require significant quantities of water, as shown by the pulse testing whose results are shown in FIG. 2, because of the retention time of acrylic acid and the slight tailing of the acrylic acid peak evident in FIG. 2. Preferably, then, the eluent is a combination of water with one or more organic solvents. Both methanol and acetone proved effective (as shown by FIGS. 3-5) in reducing the retention time of the acrylic acid peak and in reducing elution requirements overall, though those skilled in the art will be well able to identify other organic solvents that would accomplish these ends, and to optimize their use with water in the process step 16 after the manner of the examples below.

Figure 7:
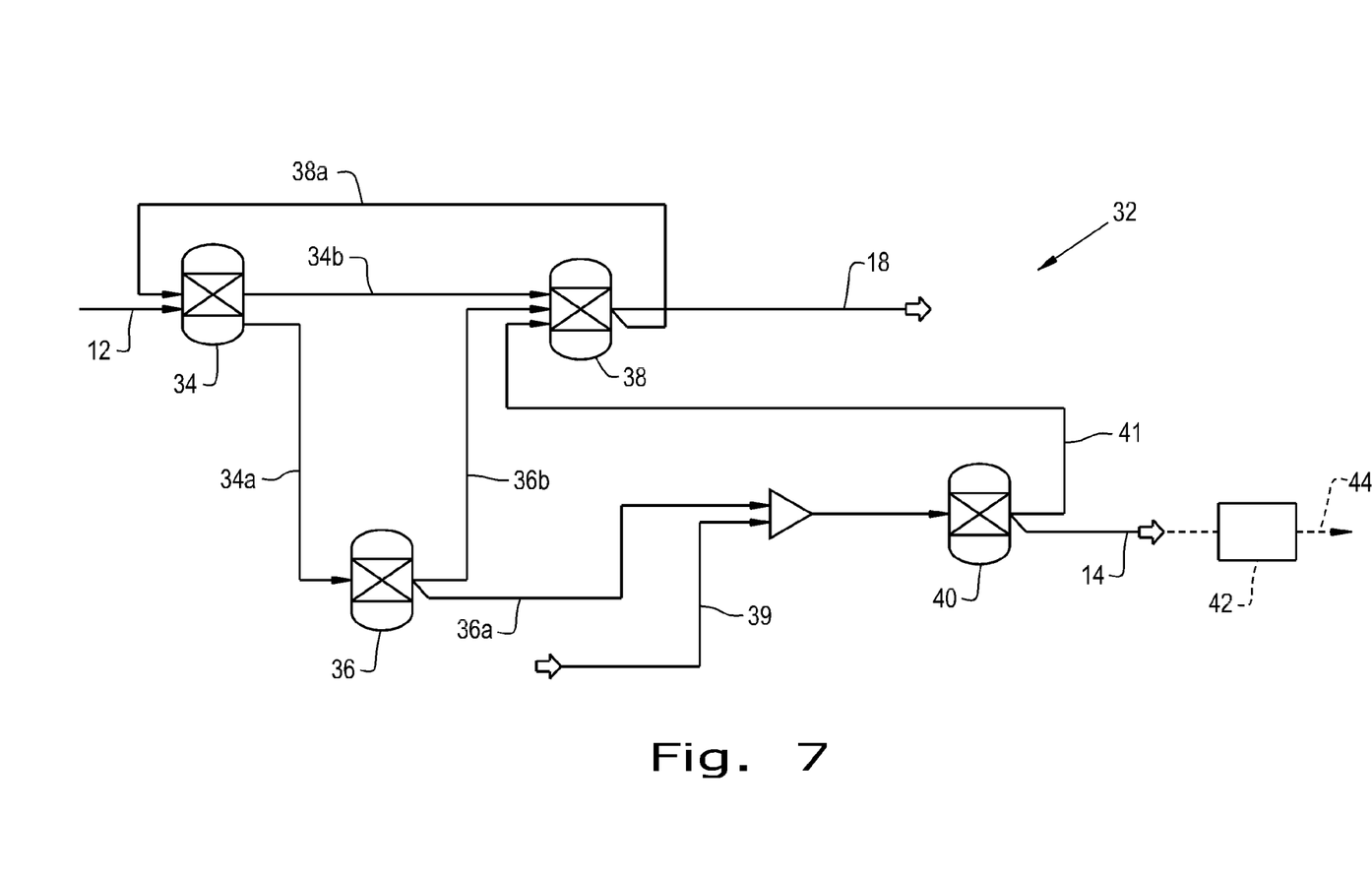
FIG. 7 schematically depicts a modeled process embodiment for removing excess propionic acid from an acrylic acid product from any of the source processes referenced in FIG. 1, using a combination of crystallization and chromatography.

In an optional further step not shown in FIG. 1, but schematically illustrated in FIG. 7 for a combined chromatography/crystallization method, residual acrylic acid remaining with the propionic acid 14 may be hydrogenated to produce additional propionic acid and thereby provide a higher purity propionic acid product. In certain embodiments, the hydrogenation can be carried out in the manner described in the above-referenced U.S. Pat. No. 8,440,859 to Dubois. It should be noted, however, that whereas Dubois contemplates that the material being hydrogenated will contain from 50 to 90 percent by weight of acrylic acid, the acrylic acid content in our propionic acid 14—whether resulting from an application of chromatographic methods or from a combination of crystallization and chromatography—will be very much less than 50 percent by weight. Accordingly, accomplishing Dubois's desired propionic acid purity of at least about 85 percent by weight, preferably at least about 95 percent by weight, and more preferably at least about 99% by weight, should ultimately be considerably easier in our process wherein, for example, the propionic acid 14 contains 7.9 percent by weight of residual acrylic acid (Example 28) rather than being mostly comprised of acrylic acid as in Dubois.

As related in U.S. Pat. No. 8,440,859 to Dubois, the hydrogenation can be carried out in the liquid or gas phase with a source of molecular hydrogen. Known methods of carrying out the hydrogenation referenced by Dubois include FR 2219927, Chemicky Prumsyl 37, pp. 651-653 (1987) and Electroanalytical Chemistry (1975), pp. 75-80. Particularly described are: a homogeneous liquid phase process using a ruthenium-phosphine complex and methanol as a solvent, carried out at approximately 60 degrees Celsius and at a pressure of approximately 3 MPa; heterogeneous gas-phase catalysis over a copper/zinc on aluminum oxide catalyst in a fixed bed, at a temperature between 250 degrees and 350 degrees Celsius and a pressure of between 1 atmosphere and 6 atmospheres; and heterogeneous catalysis over a palladium catalyst applied in the form of a liquid palladium salt solution adsorbed on a porous support, such as silicic acid or an active charcoal, the salt being subsequently reduced to form metallic platinum, at a temperature of from 20 to 80 degrees Celsius and a hydrogen pressure of from 1 to 10 atmospheres.

In an alternative optional further step, excess propionic acid 14 separated from an acrylic acid product 12 by simulated moving bed chromatography may be oxidatively dehydrogenated to provide additional acrylic acid, for example, by a catalyst and method as described in EP 2039674 B1 to Han et al, wherein a mixed metal oxide catalyst of the formula $A_aM_bN_cX_dZ_eO_f$ is used, where A is "at least one element selected from the group consisting of Mo and W; M is at least one element selected from the group consisting of V and Ce; N is at least one element selected from the group consisting of Te, Sb and Se; X is at least one element consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu; and Z is at least one element selected from the group consisting of Zn, Ga, Ir, Sm, Pd, Au, Ag, Cu, Sc, Y, Pr, Nd and Tb; and O is oxygen in oxide form and wherein, when a=1, b=0.01 to 1.0, c=0.01 to 1.0, d=0.01 to 1.0, e=0 to 0.1, and f is dependent on the oxidation state of the other elements". Preferred catalysts were "$Mo_aV_mTe_n$-$Nb_xO_o$ and $W_aV_mTe_nNb_xO_o$ wherein a, m, n, x and o [sic—f?] are as previously defined". Alternatively, a MoFe-CoO catalyst and method as described in the JP 2000053611 reference mentioned by Han et al. may be used. In another alternative embodiment, a catalyst and method as described in JP 07-330658 to Keiko (assigned to Daicel Chemical Industries Ltd) wherein propionic acid or its corresponding ester are oxidatively dehydrogenated using a catalyst of the formula $P_aMo_bV_cA_dCe_eB_fO_g$, where A is one or more of copper, arsenic, antimony, silicon, tungsten, chromium, silver and magnesium, B is one or more of potassium, rubidium, cesium and thallium, (a) is from 0.5 to 3, (c) is from 0.1 to 3, (d) is from 0 to 3, (e) is from 0.01 to 3, (f) is from 0.01 to 2 and (g) is as required when (b) is 12. In another alternative embodiment, a catalyst and process may be used as described in McEntee et al, "Selective Catalytic Oxidative-Dehydrogenation of Carboxylic Acids—Acrylate and Crotonate Formation at the Au/TiO$_2$ Interface", J. Am. Chem. Soc. Vol. 136, pp. 5116-5120 (2014), wherein a gold on titania catalyst was employed. In still another alternative embodiment, a catalyst and method may be used as described in U.S. Pat. No. 3,855,279 to Watkins, wherein (as specifically shown in Example 9) propionic acid may be oxidatively dehydrogenated to acrylic acid using a catalyst comprised of the calcined residue of the mixed phosphates of iron and lead in the presence of oxygen and at temperatures in the range of from about 250 degrees Celsius to about 600 degrees Celsius. This additional acrylic acid can likewise be processed by chromatography in the same manner as acrylic acid product(s) 12, as appropriate given any unconverted propionic acid remaining and applicable propionic acid limits for achieving a desired glacial acrylic acid product Excess propionic acid may also be removed from an acrylic acid product 12 or a plurality of such products 12 by a combination of chromatography and crystallization, as shown in one illustrative embodiment 32 (of a process step 16) that is schematically illustrated in FIG. 7. Referring now to that illustration, an acrylic acid product 12 containing excess propionic acid is in one embodiment purified in a series of melt crystallization stages indicated by reference numerals 34, 36 and 38, and through an application of chromatography to a portion or fraction of the product 12 as indicated by reference number 40.

The use of both melt and fractional crystallization for the purification of acrylic acid is very well-known and established, and various dynamic, suspension and static crystallization methods and devices are known. Melt crystallization fundamentally operates by isolating a compound from a melt by cooling and crystallizing the desired product according to the thermodynamic equilibrium of the initial system, and in the context of the present invention is used to produce an acrylic acid having a reduced propionic acid content compared to the solution of propionic acid-containing acrylic acid fed to a crystallizer, as well as a mother liquor retaining propionic acid in solution.

It is considered that any known crystallizer may be employed, and the type or size thereof is not particularly limited. Falling film crystallizers, for example, of the type sold by Sulzer Ltd., Winterthur, Switzerland, are a type of dynamic layer crystallization device presently used for purifying acrylic acid and may be used in one embodiment for melt crystallization stages 34, 36 and 38, though U.S. Pat. No. 8,440,859 to Dubois expresses a preference for a series of falling film crystallizers followed by a final static crystallizer. In most falling film crystallizers, the purified acrylic acid crystallizes on the inside surface of a tube, though a falling film crystallizer is described in Le Page Mostefa et al., "A purification route of bio-acrylic acid by melt crystallization respectful of environmental constraints", Powder Technology, vol. 255, pp. 98-102 (2014) wherein the acrylic acid crystallizes on the external surface of a tube. According to the authors, such a configuration enables a larger portion of the initial melt to be crystallized without the risk of plugging that would occur if the crystallization were on the inside surface of a tube, and higher productivity can be obtained from the crystallizer. The authors also claim other benefits from their design, including reduced cycle times compared to previously known designs. Still other crystallizer designs continue to be introduced in the literature, and may be considered for use in one or more of melt crystallization stages 34, 36 and 38, see, e.g., the hydraulic wash column described by Verdoes and Bassett, "High Purity Products by Crystallization", Specialty Chemicals, vol. 29, no. 7, pp. 32-35 (2009) and Funakoshi et al., "Influences of reflux ratio on separation and purification of acrylic acid by inclined column crystallizer", Journal of Crystal Growth 237-239, pp. 2251-2256 (2002).

Falling film crystallizations are generally carried out in a multitube exchanger, with each tube being fed continuously at its top with a liquid stream (a melt) of acrylic acid from which propionic acid is to be removed, which liquid falls as a film along the internal wall of the tube, is received at the tube bottom and recirculated at the top of the tube for as long as necessary in a closed loop for the crystallization of the desired amount of acrylic acid on the internal tube wall. Concurrently, a heat exchange fluid, typically being ethylene glycol/water or methanol/water, flows along the external wall of the tube and provides the cooling or heating necessary for the operation of each stage of a crystallization cycle, with recycling from the tube bottom to the tube top for the duration of the crystallization cycle.

Each crystallization stage 34, 36 and 38 proceeds in three phases or stages: crystallization, sweating and melting. In the crystallization stage, the temperature of the heat exchange fluid is lowered along a negative temperature gradient, starting from a temperature slightly above the crystallization temperature of the acrylic acid in the melt, typically about 14 degrees Celsius. Crystals form on the surface of the inner tube wall. When approximately 30 to 80 percent of the acrylic acid circulated has crystallized, the remaining liquid fraction—the mother liquor—is drained away and removed. In sweating, the temperature of the heat exchange fluid is raised along a positive temperature gradient in order to remove, by melting, impurities (in this case, principally propionic acid) trapped in the form of inclusions in the layer of acrylic acid crystals being formed; these inclusions occur increasingly as the layer is built up, through contact with the recirculating impure acrylic acid which is increasingly concentrated in the propionic acid as acrylic acid is crystallized out. In the melting stage, the temperature of the heat exchange liquid is rapidly increased above the melting point of acrylic acid (14 degrees Celsius) but not to an extent whereby polymerization occurs (for example, not higher than about 35 to 40 degrees Celsius), and the crystalline layer melts and is collected. Typically the crystalline layer from a first crystallizer is supplied to a second crystallizer as the melt, so that through sequenced operation higher purities can be achieved as illustrated in Example 28 below.

In the particular embodiment 32 depicted in FIG. 7, an acrylic acid composition 12 containing excess propionic acid, for example, as received from the overhead of the second distillation column in a two-column distillation section of an associated process for making acrylic acid from propane, from glycerol, from lactic acid or lactate esters, or from any combination of these processes, is conveyed to melt crystallization stage 34. In this regard, a first distillation column would be envisioned for the removal of lighter compounds such as acetic and formic acids from the crude acrylic acid product of one or more of the above-referenced processes, while the second column would perform a further distillation on the bottoms from the first, lights column. The acrylic acid composition 12 would correspond to the overheads from this second column, while the bottoms from the second column would contain as much of the propionic acid as can be practically removed by distillation alone from the crude acrylic acid product or products from one or more of the propane, glycerol and lactic acid/lactate processes.

Returning now to FIG. 7, the mother liquor 34a from the above-described sequence in stage 34 enters melt crystallization stage 36, while the crystallizate 36b from the second melt crystallization stage 36 is combined with the crystallizate 34b from the first melt crystallization stage 34, and the combined crystallizates 34b and 36b are fed to a third melt crystallization stage 38. The mother liquor 36a from the second stage 36 is combined with the propionic acid-containing bottom stream 39 from the second distillation column in a typical two-column sequence just described, and this combination is used as the feed for the chromatographic separation step 40. An acrylic acid product 41 from the preferred simulated moving bed chromatographic system in step 40 is then fed to the third melt crystallization stage 38 alongside crystallizates 34b and 36b, while the raffinate stream from chromatographic separation step 40 essentially corresponds to the excess propionic acid 14 removed from acrylic acid composition by a combination of chromatography and melt crystallization. The crystallizate from the third melt crystallization stage 38 then essentially corresponds to the reduced propionic acid content acrylic acid product 18 of schematic FIG. 1, while the mother liquor 38a is recycled back to the first melt crystallization stage 34.

In an optional further step (42), the propionic acid 14 may be further processed by hydrogenation or by oxidative dehydrogenation as previously discussed in reference to FIG. 1, to respectively convert residual acrylic acid to additional propionic acid or to convert propionic acid to additional acrylic acid (with a resultant product 44 according to which optional further process step is performed). Because acrylic acid is ordinarily expected to be present in the propionic acid 14 in comparatively minor amounts, i.e., at less than 10 percent by weight, conventionally it is expected that if the further step 42 is desirable for achieving a greater yield or higher purity of propionic acid for some use, then the step 42 will involve hydrogenation of residual acrylic acid in the propionic acid 14 to produce a propionic acid at a greater purity as product 44. U.S. Pat. No. 8,440,859 to Dubois posits a number of uses of such a propionic acid product.

This invention is further illustrated by the following non-limiting examples:

EXAMPLES

Example 1

In order to determine if simulated moving bed (SMB) chromatography could be used for the separation, a series of pulse tests were performed on the DIAION AMP-03 amphoteric ion exchange resin. The standard test procedure involved charging 100 ml of the resin to a 1.5 cm diameter glass column as a slurry in water at room temperature. The resin was then washed with 500 ml of water. Water was drained to the top of the resin, then a 6 ml pulse of feed was charged to the resin column. The liquid was again drained to the top of the resin, and 2 ml of water added. Again, the liquid was drained to the top of the resin, then about 10 ml of water was added to the head space. Water was flowed through the resin at 3 ml/minute while collecting a 6 ml fraction at intervals. The 6 ml fractions were then analyzed.

Following the above procedure, it was found as shown in FIG. 1 that both acetic and propionic acids can be separated from acrylic acid by means of SMB chromatography using an amphoteric ion exchange resin such as the DIAION AMP-03 amphoteric ion exchange resin under isocratic conditions.

Examples 2-4

The pulse test performed in Example 1 shows that the SMB chromatographic separation of acrylic acid from propionic acid is technically possible. However, the water requirements would most likely be quite significant due to the late elution and slight tailing of the acrylic acid peak. One potential solution would be to use either an organic solvent or a mixture of water and organic solvent to decrease the elution requirements. Following the above procedure, different levels of methanol and acetone were evaluated in combination with water in Examples 2-4 to see if the retention and peak shape of the acrylic acid could be improved.

The use of 5% acetone in water (Ex. 2 and FIG. 2) showed that the retention time of the acrylic acid peak could be decreased by 0.5 bed volumes and the tail decreased by about 1 bed volume, indicating that elution requirements could in fact be reduced compared to the isocratic separation in an SMB chromatographic separation.

Methanol as a co-solvent at 15% in the elution in a pulse test (Example 3 and FIG. 3) also decreased elution requirements and improved the peak shape of all of the acid peaks. Increasing the relative concentration of methanol to 50% (Example 4 and FIG. 4) significantly decreased the elution time of the acrylic acid but the peak overlap of the acrylic and propionic acid peaks increased to the point where the SMB chromatographic separation would most likely not be successful.

Examples 5-9

The pulse tests reported in Examples 1-4 confirm that SMB chromatography may be used for the separation of acrylic acid from both acetic and propionic acid using both isocratic conditions and with mixed solvents as the eluent, though because of the difference in the boiling points of acetic acid and acrylic acid, a distillative separation may be preferred as to the acetic acid byproduct. To further evaluate the performance of the various eluents in an SMB chromatographic arrangement, a 12-column carousel SMB chromatography unit was arranged in a 2-5-4-1 column arrangement employing the DIAION AMP-03 amphoteric ion exchange resin (see FIG. 5). Four individual pumps were operated independently for the desorb, enrich, feed and reload streams.

Table 1 shows a series of experiments run using the 12-column arrangement and isocratic conditions, with all flows reported being in grams/minute:

TABLE 1

| Experiment | 1 | 2 | 3 | 4 | 5 |
|---|---|---|---|---|---|
| Step Time (min) | 12 | 12 | 12 | 12 | 12 |
| Feed | 4.71 | 4.76 | 4.38 | 4.38 | 4.17 |
| Enrich | 18.35 | 18.89 | 21.04 | 16.18 | 15.5 |
| Elution | 25.26 | 28.1 | 23.33 | 20.32 | 20.67 |
| Extract | 20.92 | 22.2 | 17.29 | 20.14 | 21.17 |
| Raffinate | 9 | 10.48 | 11.04 | 4.56 | 4.17 |
| Reload | 14 | 13 | 15 | 16 | 16 |
| Zone I flow | 39.26 | 41.1 | 38.33 | 36.32 | 36.67 |
| Zone II flow | 18.34 | 18.9 | 21.04 | 16.18 | 15.5 |
| Zone III flow | 23.05 | 23.66 | 25.42 | 20.56 | 19.67 |
| Zone IV flow | 14 | 13 | 15 | 16 | 16 |
| % Acrylic Recovery | 95.6 | 99.6 | 57 | 88.4 | 94.9 |
| % Acrylic Purity | 99.3 | 99.2 | >99.9 | 99.3 | 99.1 |
| Acrylic Conc. (g/L) | 28.7 | 25.5 | 21.4 | 30.3 | 31.4 |
| Propionic Conc. (g/L) | 0.2 | 0.2 | 0 | 0.2 | 0.3 |

As the data in Table 1 show, a 99+ percent pure acrylic acid product was realized relative to propionic acid at a recovery of more than 95 percent. The feed contained from 100-150 g/liter of acrylic acid combined with from 7-15 g/liter of propionic acid.

Examples 10-18

Table 2 shows a series of experimental runs using the 12-column arrangement but with 10% acetone in an acetone/water combination eluent:

TABLE 2

| | Experiment | | | | | | | | |
|---|---|---|---|---|---|---|---|---|---|
| | 1 | 2 | 3 | 4 | 5 | 6 | 7 | 8 | 9 |
| Step Time (min) | 12 | 1 | 1 | 1 | 1 | 1 | 12 | 1 | 12 |
| Feed | 4.79 | 4.83 | 4.75 | 4.86 | 4.76 | 5 | 5 | 5 | 5 |
| Enrich | 13.96 | 15 | 14.58 | 15.56 | 15.71 | 15.76 | 15.42 | 15.13 | 14.58 |
| Elution | 15.07 | 14.33 | 13.5 | 14.14 | 14.6 | 14.68 | 14.6 | 14.71 | 14.69 |
| Extract | 16.11 | 15.33 | 14.92 | 14.58 | 14.88 | 14.92 | 15.19 | 15.58 | 16.11 |
| Raffinate | 3.54 | 3.75 | 3.42 | 4.42 | 4.36 | 4.45 | 4.09 | 4 | 3.72 |
| Reload | 15 | 1 | 16 | 16 | 1 | 16 | 1 | 1 | 16 |
| Zone I flow | 30.07 | 30.33 | 29.5 | 30.14 | 30.6 | 30.68 | 30.6 | 30.71 | 30.69 |
| Zone II flow | 13.96 | 15 | 14.58 | 15.56 | 15.72 | 15.76 | 15.41 | 15.13 | 14.58 |
| Zone III flow | 18.75 | 19.83 | 19.33 | 20.42 | 20.48 | 20.76 | 20.41 | 20.13 | 19.58 |
| Zone IV flow | 15 | 1 | 1 | 1 | 1 | 1 | 1 | 1 | 16 |
| % Acrylic Recovery | 98.38 | 96.7 | 99.05 | 98.2 | 97.1 | 50.33 | 58.5 | 74.4 | 90.1 |
| % Acrylic Purity | 92.7 | 95.9 | 99.3 | 99.4 | 99.7 | 99.6 | 99.6 | 99.3 | 98.7 |
| Acrylic Conc. (g/L) | 41.9 | 35 | 27.1 | 31.4 | 37.5 | 25 | 28 | 30 | 39 |
| Propionic Conc (g/L) | 3.3 | 1.5 | 0.2 | 0.2 | 0.1 | 0.1 | 0.1 | 0.2 | 0.5 |

As expected from the pulse tests, when changing the elution solvent to include 10% acetone the desired yield and purities were achieved with a significant decrease in elution requirements from Examples 5-9, from 5:1 elution:feed for the isocratic separation to 3:1 for the mixed acetone/water eluent. This results in increased extract concentrations and decreased evaporation. Solvent recovery costs may offset these benefits to an extent.

Examples 19-27

Table 3 shows a series of experimental runs conducted with 25% methanol as a co-solvent:

TABLE 3

| | Experiment | | | | | | | | |
|---|---|---|---|---|---|---|---|---|---|
| | 1 | 2 | 3 | 4 | 5 | 6 | 7 | 8 | 9 |
| Step Time (min) | 12 | 12 | 12 | 12 | 12 | 12 | 12 | 12 | 12 |
| Feed | 5 | 5 | 4.42 | 4.54 | 4.58 | 4.38 | 4.49 | 4.5 | 4.39 |
| Enrich | 13.23 | 14.91 | 15.25 | 12.69 | 13.44 | 13.75 | 15.19 | 14.94 | 15.68 |
| Elution | 15.15 | 14.93 | 15 | 14.83 | 14.21 | 14.1 | 15.09 | 14.61 | 14.91 |
| Extract | 17.92 | 16.02 | 15.75 | 18.15 | 16.77 | 16.35 | 15.9 | 15.67 | 15.23 |
| Raffinate | 1.92 | 3.63 | 3.42 | 0.67 | 1.6 | 1.81 | 3.36 | 3.11 | 4 |
| Reload | 16 | 16 | 16 | 16 | 16 | 16 | 16 | 16 | 16 |
| Zone I flow | 31.15 | 30.93 | 31 | 30.83 | 30.21 | 30.1 | 31.09 | 30.61 | 30.91 |
| Zone II flow | 13.23 | 14.91 | 15.25 | 12.69 | 13.44 | 13.75 | 15.19 | 14.94 | 15.68 |
| Zone III flow | 18.23 | 19.91 | 19.67 | 17.22 | 18.02 | 18.13 | 19.68 | 19.44 | 20.07 |
| Zone IV flow | 16 | 16 | 16 | 16 | 16 | 16 | 16 | 16 | 16 |
| % Acrylic Recovery | 99.2 | 67.1 | 63.6 | 98.7 | 96.1 | 93.4 | 98.4 | 86.4 | 94.87 |
| % Acrylic Purity | 98.7 | 99.3 | 100 | 96.4 | 98.7 | 98.4 | 97.4 | 99.5 | 99.3 |
| Acrylic conc (g/l) | 37.3 | 30 | 28 | 37 | 31 | 37 | 37.5 | 38 | 41.3 |
| Propionic conc (g/l) | 0.5 | 0.2 | 0 | 1.4 | 0.4 | 0.6 | 1 | 0.2 | 0.3 |

Again, the desired yield and purities were able to be achieved, with a significant decrease in elution requirements compared to isocratic operation.

Example 28

A process according to FIG. 7 (not including the optional further processing of propionic acid 14) was modeled using commercially available ASPENPLUS (Version 8.2) process modeling software from Aspen Technology, Inc., Burlington, Mass., following a series of melt crystallization experiments conducted on various combinations of acrylic acid and propionic acid to construct an equilibrium phase diagram and determine the eutectic composition between acrylic acid and propionic acid, and further based on the chromatographic testing summarized above. Results of the modeling are shown below in Table 4, for an incoming acrylic acid composition 12 and a propionic acid-containing bottoms stream 39 from the second distillation column in a preceding process for making biobased acrylic acid generally according to U.S. Pat. No. 4,786,756 to Paparizos et al.

TABLE 4

| | Flow# | | | | | | | | | |
|---|---|---|---|---|---|---|---|---|---|---|
| | 39 | 12 | 34b | 18 | 36b | 34a | 38a | 36a | 41 | 14 |
| Mass flow, kg/hr | 2.701 | 7.307 | 7.718 | 8.378 | 2.578 | 3.976 | 4.386 | 1.398 | 2.468 | 1.63 |
| Vol. flow, l/min | 0.043 | 0.114 | 0.121 | 0.131 | 0.04 | 0.062 | 0.069 | 0.022 | 0.039 | 0.026 |
| Density, kg/m$^3$ | 1044.911 | 1066.582 | 1067.023 | 1067.333 | 1066.776 | 1065.411 | 1066.249 | 1062.967 | 1066.946 | 1034.805 |
| Mass fraction | | | | | | | | | | |
| Acrylic | 0.478 | 0.984 | 0.991 | 0.997 | 0.987 | 0.961 | 0.976 | 0.913 | 0.988 | 0.079 |
| Propionic | 0.522 | 0.016 | 0.009 | 0.003 | 0.013 | 0.039 | 0.024 | 0.087 | 0.012 | 0.921 |

Every document cited herein, including any cross-referenced or related patent or application, is hereby incorporated herein by reference in its entirety unless expressly excluded or otherwise limited.

Further, while particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A process for chromatographically separating propionic acid from an acrylic acid composition containing propionic acid, comprising contacting the acrylic acid composition with an amphoteric ion exchange resin having a quaternary ammonium group and a carboxy group incorporated on a cross-linked polystyrene frame and eluting propionic acid into a raffinate such that a reduced propionic acid acrylic acid product is recovered in an extract.

2. A process according to claim 1, wherein sufficient propionic acid is eluted in the raffinate such that the reduced propionic acid acrylic acid product contains less than 3000 parts per million of propionic acid.

3. A process according to claim 2, wherein sufficient propionic acid is removed in the raffinate to provide a reduced propionic acid acrylic acid product containing less than 1000 parts per million of propionic acid.

4. A process according to any of claims 1-3, which is conducted in a series of columns and with an eluent caused to pass through the columns as a simulated moving bed.

5. A process according to claim 4, wherein the acrylic acid composition contains at least about 3000 parts per million by weight of propionic acid.

6. A process according to claim 5, wherein the acrylic acid composition contains at least about 5000 parts per million by weight of propionic acid.

7. A process according to claim 1, wherein the eluent is water and the chromatographic process is carried out isocratically.

8. A process according to claim 1, wherein the eluent fed into the process is a combination of water and an organic solvent.

9. A process according to claim 8, wherein the organic solvent is methanol.

10. A process according to claim 9, wherein the eluent supplied to the process includes at least about 15 percent up to about 50 percent of methanol with the remainder of water.

11. A process according to claim 8, wherein the organic solvent is acetone.

12. A process according to claim 11, wherein the eluent supplied to the process includes at least about 5 percent of acetone.

13. A process according to claim 12, wherein the eluent supplied to the process includes at least about 10 percent of acetone.

14. A process for chromatographically separating propionic acid esters from an acrylate ester composition containing propionic acid esters, comprising contacting the acrylate ester composition with an amphoteric ion exchange resin having a quaternary ammonium group and a carboxy group incorporated on a cross-linked polystyrene frame, and eluting propionic acid esters into a raffinate such that a reduced propionic acid ester acrylate ester product is recovered in an extract.

15. A process according to claim 1, further comprising hydrogenating residual acrylic acid in the raffinate in the presence of a source of hydrogen to form propionic acid therefrom.

16. A process according to claim 1, further comprising oxidatively dehydrogenating propionic acid in the raffinate to form additional acrylic acid therefrom.

17. A process according to claim 14, further comprising hydrogenating residual acrylate esters in the raffinate in the presence of a source of hydrogen to form propionate esters therefrom.

18. A process according to claim 14, further comprising oxidatively dehydrogenating propionic acid esters in the raffinate to form additional acrylate esters therefrom.

19. A process for making a reduced propionic acid content acrylic acid product, comprising removing propionic acid from an acrylic acid composition containing propionic acid both by melt crystallization and by adsorbing propionic acid onto an amphoteric ion exchange resin having a quaternary ammonium group and a carboxy group incorporated on a cross-linked polystyrene frame.

20. A process according to claim 19, further comprising producing the acrylic acid composition containing propionic acid at least in part by performing a catalytic oxidation of propane with an oxygen source, in the presence of a catalyst and under conditions which are suitable for carrying out the oxidation.

21. A process according to claim 19 or 20, further comprising producing the acrylic acid composition containing propionic acid at least in part by carrying out a dehydration of glycerol to yield acrolein and then oxidizing acrolein to provide acrylic acid.

22. A process according to claim 21, further comprising producing the acrylic acid composition containing propionic acid at least in part by dehydration of lactic acid and/or one or more lactate esters.

23. A process according to claim 19 or 20, further comprising producing the acrylic acid composition containing propionic acid at least in part by dehydration of lactic acid and/or one or more lactate esters.

* * * * *